United States Patent
Kertser

(10) Patent No.: US 10,953,189 B2
(45) Date of Patent: Mar. 23, 2021

(54) PNEUMATIC SYSTEM FOR CONTROLLED OXYGEN DELIVERY

(71) Applicant: ORIDION MEDICAL 1987 LTD., Jerusalem (IL)

(72) Inventor: Michael Kertser, Jerusalem (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 274 days.

(21) Appl. No.: 15/874,105

(22) Filed: Jan. 18, 2018

(65) Prior Publication Data

US 2018/0207391 A1    Jul. 26, 2018

Related U.S. Application Data

(60) Provisional application No. 62/448,471, filed on Jan. 20, 2017.

(51) Int. Cl.
*A61M 16/20*  (2006.01)
*A61M 16/10*  (2006.01)
*A61M 16/06*  (2006.01)

(52) U.S. Cl.
CPC ...... *A61M 16/207* (2014.02); *A61M 16/0672* (2014.02); *A61M 16/101* (2014.02); *A61M 16/1005* (2014.02); *A61M 2016/103* (2013.01); *A61M 2016/1025* (2013.01); *A61M 2202/0208* (2013.01); *A61M 2230/432* (2013.01)

(58) Field of Classification Search
CPC .. A61M 16/20; A61M 16/208; A61M 16/209; A61M 16/201; A61M 16/2017; A62B 9/02; A62B 9/027; A62B 7/04
See application file for complete search history.

(56) References Cited

U.S. PATENT DOCUMENTS

| | | | | |
|---|---|---|---|---|
| 5,360,000 | A * | 11/1994 | Carter | A61M 16/20 128/204.26 |
| 6,253,764 | B1 * | 7/2001 | Calluaud | A61M 16/20 128/204.18 |
| 6,364,161 | B1 | 4/2002 | Pryor | |
| 6,425,396 | B1 | 7/2002 | Adriance et al. | |
| 2002/0112722 | A1 | 8/2002 | Carter | |
| 2005/0028816 | A1 * | 2/2005 | Fishman | A61M 16/0051 128/200.24 |
| 2006/0201504 | A1 * | 9/2006 | Singhal | A61M 16/00 128/204.18 |
| 2006/0219245 | A1 | 10/2006 | Holder | |
| 2013/0192597 | A1 | 8/2013 | McKinnon et al. | |

OTHER PUBLICATIONS

International Search Report and Written Opinion for PCT Application No. PCT/IL2018/050069 dated Apr. 10, 2018; 11 pgs.

* cited by examiner

*Primary Examiner* — Margaret M Luarca
(74) *Attorney, Agent, or Firm* — Cantor Colburn LLP

(57) ABSTRACT

A pneumatic system for delivering oxygen to a subject, including an oxygen supply channel having an inlet, a patient delivery outlet and an exhaust; and a flow control element configured to control the flow from the oxygen inlet to the patient delivery outlet, or to the exhaust; wherein inhalation by the patient causes the flow control element to assume a first position, allowing oxygen to flow from the oxygen inlet to the patient delivery outlet; and wherein exhalation by the patient causes the flow control element to assume a second position, directing oxygen flow from the oxygen inlet to the exhaust.

14 Claims, 2 Drawing Sheets

PNEUMATIC SYSTEM FOR CONTROLLED OXYGEN DELIVERY

This application claims the benefit of U.S. Provisional Application Ser. No. 62/448,471 filed Jan. 20, 2017, the content of which is incorporated herein by reference in its entirety for all purposes.

TECHNICAL FIELD

The present disclosure generally relates to the field of breath monitoring, and specifically to $CO_2$ sampling alongside oxygen delivery.

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

For some breathing disorders, treatment includes oxygen delivery. While oxygen is being delivered, it is often desired to obtain measurements of exhaled breath in order to evaluate the patient's condition. During exhalation, there is no need for oxygen supply. In fact, supplying oxygen during inhalation increases the risk of sample dilution inside the oxygen mask, in case of capnography measurement of the exhaled $CO_2$. The pneumatic system for oxygen supply, disclosed herein, enables synchronizing oxygen supply with inhalation, thereby enabling reliable capnometric measurements during high flow oxygen supply.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Monitoring exhaled breath is often impaired due to dilution of the exhaled breath by the delivered oxygen (or other medicinal gas mixture). The pneumatic system for oxygen supply, disclosed herein, recognizes initiation of exhalation and redirects the oxygen flow away from the oxygen supply mask. The system may use changes in pneumatic pressure caused by the patient's inhalation/exhalation to control the flow of oxygen towards/away from the oxygen mask, as further described herein below.

The driving element of the system may be a pneumatic actuator. When the patient exhales, a piston reaches a position to prevent incoming oxygen flow from being supplied to the patient, thereby ensuring that the measurement of $CO_2$ might be performed without dilution of the exhaled breath.

According to some embodiments, there is provided a pneumatic system for delivering oxygen to a patient. The system may include an oxygen supply channel having an oxygen inlet, a patient delivery outlet, an exhaust, and a flow control element configured to control the flow from the oxygen inlet to the patient delivery outlet or to the exhaust.

According to some embodiments, inhalation by the patient causes the flow control element to assume a first position to direct oxygen to flow from the oxygen inlet to the patient delivery outlet. According to some embodiments, exhalation by the patient causes the flow control element to assume a second position, directing oxygen flow from the oxygen inlet to the exhaust. According to some embodiments, the flow control element may be or include a piston. According to some embodiments, the pneumatic system may be configured for connection to an oxygen delivery mask and/or to a breath sampling cannula. According to some embodiments, the pneumatic system may further include a pneumatic chamber. According to some embodiments, inhalation by the patient reduces a pressure within the pneumatic chamber to a first pressure value. According to some embodiments, exhalation by the patient increases the pressure within the pneumatic chamber to a second pressure value. According to some embodiments, the second pressure value is larger than the first pressure value. According to some embodiments, when the pressure within the pneumatic chamber reaches the second pressure value, the flow control element is moved to the second position.

According to some embodiments, the pneumatic chamber may include a nozzle and a sliding cap. According to some embodiments, the sliding cap may be configured to slide between a first position and a second position, thereby increasing/reducing a gap in the nozzle respectively. According to some embodiments, inhalation by the patient may cause the sliding cap to be sucked into its first position, thereby increasing the gap of the nozzle and reducing the pressure within the pneumatic chamber.

According to some embodiments, the oxygen may be supplied at a flow rate above 10 LPM.

According to some embodiments, the pneumatic system may include a control unit configured to detect the position of the flow control element and to provide a signal indicative of the position. According to some embodiments, the control unit may include a processor. For example, the pneumatic system may include a pressure sensor that may measure the pressure within a pneumatic chamber of the pneumatic system. The pressure sensor may transmit a signal to the control unit, which may determine the position of the flow control element based on the pressure within the pneumatic chamber. In other embodiments, the pneumatic system may include an optical sensor, a flow sensor, or any other suitable sensor in addition to or in lieu of the pressure sensor to determine a position of the flow control element.

According to some embodiments, there is provided an oxygen delivery system including an oxygen delivery mask and a pneumatic system configured to control delivering oxygen to the oxygen delivery mask. According to some embodiments, the pneumatic system may include an oxygen supply channel comprising an oxygen inlet, a patient delivery outlet in fluid flow communication with the oxygen delivery mask, an exhaust, and a flow control element, where the flow control element may be configured to control the flow from the oxygen inlet to the patient delivery outlet or to the exhaust.

According to some embodiments, inhalation by the patient may cause the flow control element to assume a first position to allow oxygen to flow from the oxygen inlet to the patient delivery outlet and from there to the oxygen delivery mask. According to some embodiments, exhalation by the patient may cause the flow control element to assume a second position to direct oxygen flow from the oxygen inlet to the exhaust, thereby preventing it from reaching the oxygen delivery mask. According to some embodiments, the flow control element may include a piston.

According to some embodiments, the oxygen delivery system may include a pneumatic chamber. According to some embodiments, inhalation by the patient may reduce a pressure within the pneumatic chamber to a first pressure value. According to some embodiments, exhalation by the patient may increase the pressure within the pneumatic chamber to a second pressure value. According to some embodiments, the second pressure value is larger than the first pressure value. According to some embodiments, when the pressure within the pneumatic chamber reaches the second pressure value, the flow control element is moved into the second position.

According to some embodiments, the oxygen delivery system may further include a control unit (e.g., having a sensor) configured to detect the position of the flow control element. According to some embodiments, the control unit may be further configured to provide a signal indicative of the position of the flow control element to a breath monitor. According to some embodiments, the control unit may include a processor. According to some embodiments, the oxygen delivery system may include a capnograph.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1A:
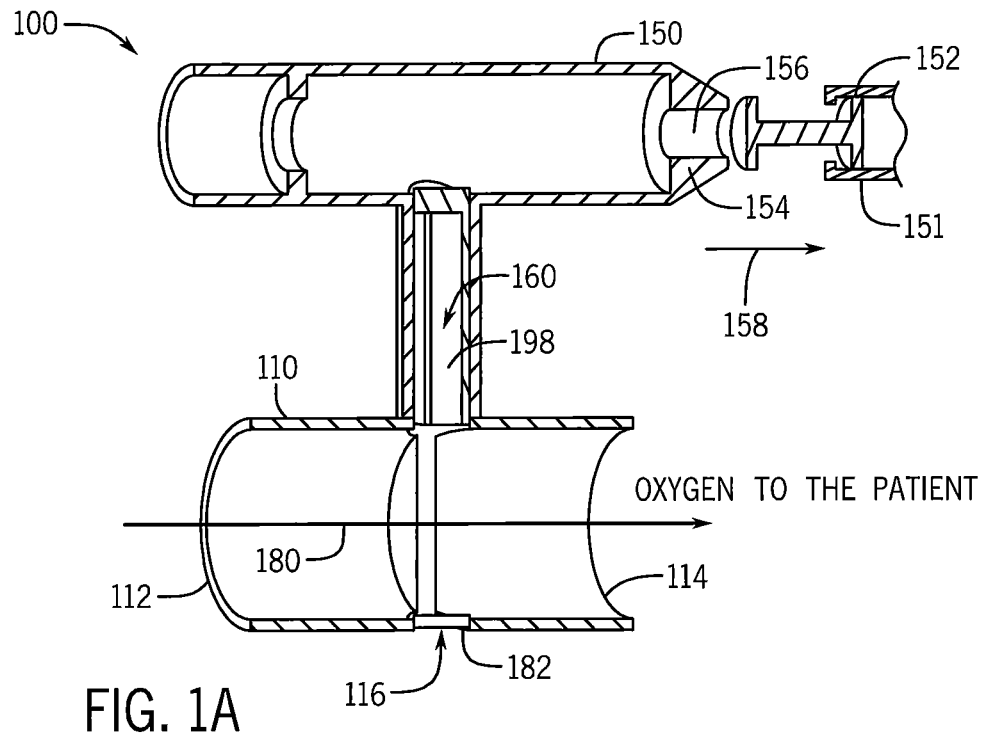
FIG. 1A shows a partially cut-away side view of a pneumatic system for oxygen delivery in an inhalation mode, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. Additionally, it is to be explicitly understood that any combination of any one or more of the disclosed embodiments may be applicable and is within the scope of the disclosure.

According to some embodiments, there is provided a pneumatic system for delivering oxygen to a patient, the system comprising an oxygen supply channel comprising an oxygen inlet, a patient delivery outlet, an exhaust, and a flow control element configured to control the flow of oxygen (or other medicinal gas or mixture of gases) from the oxygen inlet to the patient delivery outlet, or to the exhaust.

As used herein, the term "pneumatic system" may refer to a system utilizing or powered by pressurized air, e.g. a system utilizing changes in pressure that result when a fluid (e.g. a gas) flows through a constricted section of a pipe, e.g. a system utilizing the Venturi Effect. According to some embodiments, the term may refer to a system utilizing pressure changes caused by a subject's breathing to control its mode of operation.

As used herein, the term "inlet" may refer to part of the oxygen supply channel receiving oxygen (or other medicinal gas) directly from an oxygen supply or from an oxygen supply tube.

As used herein, the term "patient delivery outlet" may refer to part of the oxygen supply channel being directly or indirectly in fluid flow communication with a patient's breathing organs. According to some embodiments, the patient delivery outlet may be configured to deliver the oxygen (or other medicinal gas) directly to the patient. According to some embodiments, the patient delivery outlet may be directly or indirectly connected to an oxygen supply tube of a nasal/oral cannula and to deliver the oxygen (or other medicinal gas mixture) thereto. According to some embodiments, the patient delivery outlet may be directly or indirectly connected to an oxygen delivery mask and to deliver the oxygen (or other medicinal gas mixture) thereto.

As used herein, the term "exhaust" may refer to an outlet of the oxygen supply channel directing the flow of oxygen (or other medicinal gas mixture) away from the patient. According to some embodiments, the exhaust may redirect the oxygen back to the oxygen supply. According to some embodiments, the exhaust may release the oxygen to the surrounding air.

As used herein, the term "flow control element" may refer to any element configured to control the flow of oxygen (or other medicinal gas mixture) from the oxygen inlet to the patient delivery outlet or from the inlet to the exhaust, based on the pneumatics of breathing. According to some embodiments, the flow control element may include a piston. According to some embodiments, inhalation by the patient may cause the flow control element to assume a first position to allow oxygen to flow from the oxygen inlet to the patient delivery outlet. According to some embodiments, exhalation by the patient causes the flow control element to assume a second position to direct oxygen flow from the oxygen inlet to the exhaust.

As used herein, the terms "patient" and "subject" may be used interchangeably and may refer to any individual undergoing breath monitoring while being supplied with oxygen or other medicinal gas.

According to some embodiments, the pneumatic system may include a pneumatic chamber. According to some embodiments, inhalation by the patient may cause pressure within the pneumatic chamber to reach a first pressure value. According to some embodiments, exhalation by the patient may cause pressure within the pneumatic chamber to reach a second pressure value. According to some embodiments, the second pressure value may be larger than the first pressure value.

According to some embodiments, when the pressure within the pneumatic chamber reaches the second pressure value, the flow control element may be moved to its second position, thereby causing the flow of oxygen to be redirected from the oxygen delivery outlet to the exhaust and thus preventing exhaled air from being diluted by the delivered gas (e.g., because the flow control element blocks the flow of oxygen from the oxygen inlet to the patient delivery outlet).

According to some embodiments, the pneumatic chamber may include a nozzle having a sliding cap, the sliding cap configured to slide between a first position and a second position, thereby increasing/reducing a gap of the nozzle, respectively. When the gap closes and/or decreases, the pressure within the pneumatic chamber increases, thereby causing the flow control element to change its position from its first position, in which oxygen is allowed to flow from the inlet to the patient delivery outlet, to its second position, in which oxygen flow is redirected to the exhaust.

As used herein, the terms "sliding cap" and "drossel" may be used interchangeably and may refer to any element, having any size and shape, configured to changes its position due to a patient's inhalation/exhalation and to cause the pressure to change within the pneumatic chamber as a result thereof. According to some embodiments, inhalation by the patient causes the sliding cap to be sucked into its first position, thereby increasing the gap of the nozzle. The enlarged gap reduces the pressure within the pneumatic camber and, as a result, causes the flow control element to assume an open position (e.g., first position), allowing oxygen flow toward the patient delivery outlet.

According to some embodiments, the pneumatic system may be configured to generate and/or provide a signal to a breath monitor, such as, but not limited to, a capnograph, the signal being indicative of the pneumatic system being in exhalation/inhalation mode (e.g., a control unit includes a sensor configured to detect a position of the flow control element, wherein the flow control element is in a closed position in the exhalation mode and in an open position in the inhalation mode). According to some embodiments, the exhaled breath may be monitored during exhalation mode only. This may advantageously enable a power save mode of operation of the monitor. For example, in the power save mode, the monitor may cut off a supply of oxygen to an oxygen delivery channel of the pneumatic system. Additionally, the power save mode may be enabled during the inhalation mode by turning off sampling and monitoring of the patient's breath. Alternatively, the exhaled breath may be monitored continuously, optionally while taking into consideration the timing of the oxygen supply.

According to some embodiments, the pneumatic system may be configured to operate with oxygen flows of above 5 liters per minute (LPM), above 6 LPM, above 10 LPM, or above 15 LPM. Each possibility may be a separate embodiment.

According to some embodiments, there is provided an oxygen delivery system including an oxygen delivery mask and a pneumatic system configured to control the delivery of oxygen (or other medicinal gas) to the oxygen delivery mask.

According to some embodiments, the pneumatic system includes an oxygen supply channel having an inlet, a patient delivery outlet in fluid flow communication with the oxygen delivery mask, and an exhaust, as described herein.

According to some embodiments, the pneumatic system may include a flow control element configured to control the flow of oxygen from the oxygen inlet to the patient delivery outlet, or to the exhaust, as described herein.

According to some embodiments, inhalation by the patient causes the flow control element to assume a first position to allow oxygen to flow from the oxygen inlet to the patient delivery outlet and to the oxygen delivery mask. According to some embodiments, exhalation by the patient causes the flow control element to assume a second position to direct oxygen flow from the oxygen inlet to the exhaust, thereby preventing it from reaching the oxygen delivery mask.

According to some embodiments, the oxygen delivery system may include a breath gas monitor such as, but not limited to, a capnograph. According to some embodiments, the pneumatic system may be configured to generate and/or provide a signal to the breath monitor indicative of the pneumatic system being in exhalation/inhalation mode. According to some embodiments, the exhaled breath may be monitored during exhalation mode only. This may enable a power save mode of operation of the monitor. Alternatively, the exhaled breath may be monitored continuously, optionally while taking into consideration the timing of the oxygen supply.

Figure 1B:
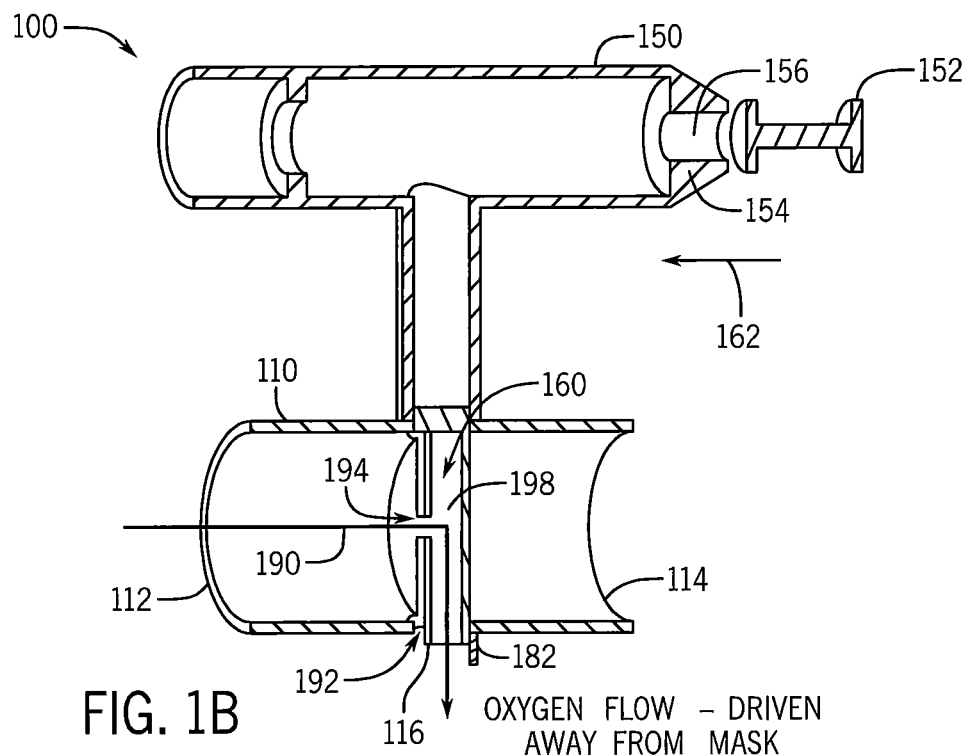
FIG. 1B shows a partially cut-away side view of a pneumatic system for oxygen delivery in an exhalation mode, according to some embodiments.

Reference is now made to FIG. 1A and FIG. 1B, which shows a side view of a pneumatic system 100 for oxygen delivery during inhalation ("inhalation mode") and exhalation ("exhalation mode"), respectively. The pneumatic system 100 includes an oxygen supply channel 110 having an inlet 112, a patient delivery outlet 114, and an exhaust 116. The pneumatic system 100 further includes a pneumatic chamber 150. The pneumatic chamber 150 includes a sliding cap 152 configured to slide relative to a nozzle 154 of the pneumatic chamber 150. An external holder 151 may be used to secure and hold the sliding cap 152 to the pneumatic system 100 in a manner that the clearance between the sliding cap 152 and the nozzle 154 controls amplification of pressure inside the pneumatic chamber 150. During inhalation, the sliding cap 152 is sucked toward the patient and away from the pneumatic chamber 150 in a direction 158 (see FIG. 1A), thereby increasing a gap 156 in the pneumatic chamber 150, and consequently the pressure within the pneumatic chamber 150 is reduced to a first pressure value. During exhalation, sliding cap 152 is pushed away from the patient and toward the pneumatic chamber 150 in a direction 162 (see FIG. 1B), thereby reducing gap 156 in the pneumatic chamber 150, and causing the pressure within pneumatic chamber 150 to increase to a second pressure value.

The pneumatic chamber 150 further includes a piston 160 configured to serve as a flow control element. The piston 160 assumes a first, open position, depicted in FIG. 1A, during inhalation, when the pressure within the pneumatic chamber 150 is at the lower first pressure value. In the first, open position of the piston 160, the flow of oxygen within the oxygen supply channel 110 is unhindered, generating a flow path from inlet 112 to patient delivery outlet 114, illustrated by arrow 180, whereas exhaust 116 is closed off by a flap 182.

During exhalation, when the pressure in pneumatic chamber 150 increases to the second pressure value, the piston 160 is pushed into its second, closed position within the oxygen supply channel 110, closing off the patient delivery outlet 114. As a result of the piston 160 being in its closed position, the flow of oxygen from the patient inlet 112 to the patient delivery outlet 114 is obstructed and the flow of oxygen is instead redirected to the exhaust 116, which is now open, as depicted in FIG. 1B arrow 190, thus enabling substantially undiluted $CO_2$ sampling during patient exhalation. For example, in the second, closed position a portion of the piston 160 extends through an opening 192 of the exhaust 116, thereby pushing the flap 182 away from the oxygen supply channel 110. In certain embodiments, the flap 182 may include a hinge that allows the flap 182 to rotate in a manner that opens and closes the exhaust 116 based on the position of the piston 160. The piston 160 may include an opening 194 that is fluidly coupled to a channel 198 within the piston 160. The channel 198 redirects the flow of the oxygen 190 through the exhaust 116.

FIG. 1A and FIG. 1B depict one configuration of the pneumatic system, disclosed herein. It is understood that other configurations utilizing the pneumatics of breathing are also possible and within the scope of the present disclosure. For example, in FIG. 1A and FIG. 1B a decrease in the pressure within pneumatic chamber 150 causes the elements of the system to be arranged such that oxygen is allowed to flow toward the patient delivery outlet 114. An alternative configuration, in which an increase within the pneumatic chamber 150 allows oxygen to flow toward the patient delivery outlet 114, is also envisaged and within the scope of this disclosure.

Figure 2A:
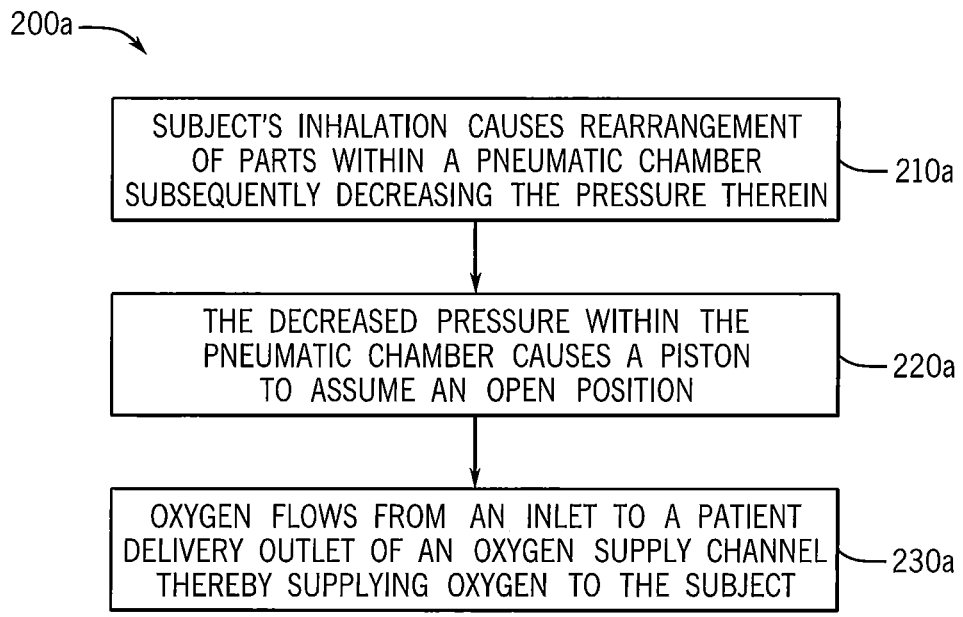
FIG. 2A is an illustrative flowchart of the operation of the pneumatic system of FIG. 1A in its inhalation mode.

Reference is now made to FIG. 2A, which is an illustrative flowchart 200a of the operation of the pneumatic system disclosed herein during inhalation. When a subject inhales (Step 210a) through a tube connected to a pneumatic chamber, a rearrangement of parts takes place, causing the pressure within the pneumatic chamber to decrease. For example, the pneumatic chamber may include a sliding cap, which increases a gap of a nozzle within the pneumatic chamber when sucked toward the patient, thereby effecting the decrease in the pressure therein. As a result of the low pressure within the chamber, a piston, configured to control the flow of oxygen from an inlet of an oxygen supply channel to a patient delivery outlet, or from the inlet to an exhaust, is sucked toward the pneumatic chamber and assumes an open position (Step 220a). In the open position of the piston, oxygen is allowed to flow from the inlet to the patient delivery outlet of the oxygen supply channel and from there to be delivered to the patient, for example, through an oxygen delivery mask (Step 230a).

Figure 2B:
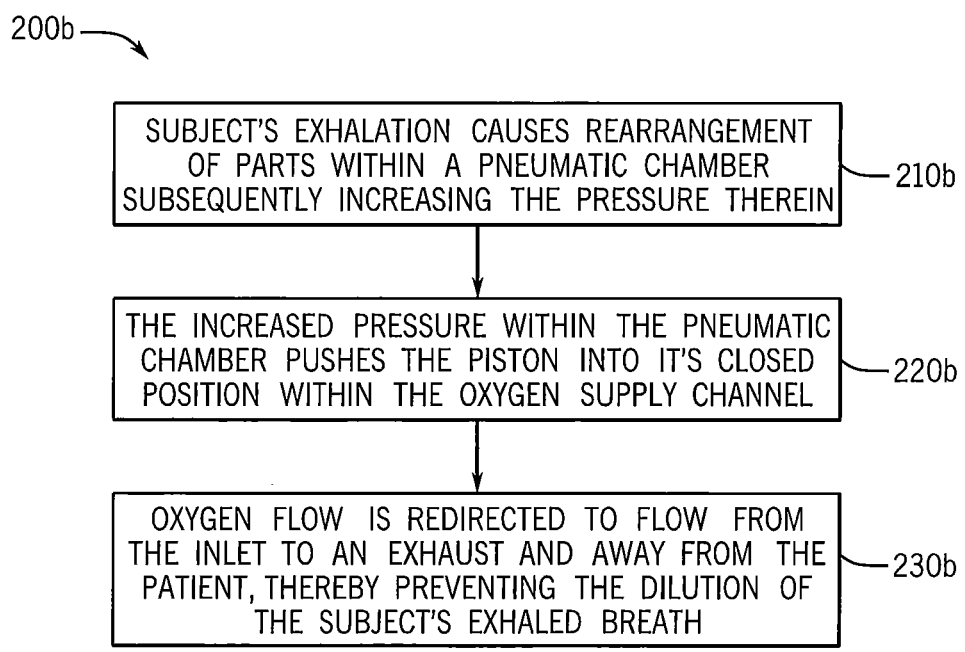
FIG. 2B is an illustrative flowchart of the operation of the pneumatic system of FIG. 1B in its exhalation mode.

Reference is now made to FIG. 2B, which is an illustrative flowchart 200b of the operation of the pneumatic system disclosed herein during exhalation. When a subject inhales (Step 220b) through a tube connected to a pneumatic chamber, a rearrangement of parts takes place causing the pressure within the pneumatic chamber to increase. For example, the pneumatic chamber may include a sliding cap, which reduces the size of a gap of a nozzle within the pneumatic chamber when exhaled air pushes sliding cap away from the subject, thereby effecting the increase in the pressure therein. As a result of the increased pressure within the chamber, the piston, configured to control the flow of oxygen from an inlet of an oxygen supply to a patient delivery outlet, or from the inlet to an exhaust, is pushed toward the oxygen supply channel and assumes a closed position (Step 220b). In the closed position of the piston, oxygen is redirected to flow from the inlet to the exhaust of the oxygen supply channel (Step 230b), thereby preventing the subject's exhaled breath from being diluted by oxygen delivered to the patient.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A pneumatic system for delivering oxygen to a patient, the system comprising:
  an oxygen supply channel comprising an inlet, a patient delivery outlet and an exhaust;
  a flow control element configured to control the flow from the inlet to said patient delivery outlet or to the exhaust, wherein inhalation by the patient causes the flow control element to assume a first position to allow oxygen to flow from the inlet to the patient delivery outlet and wherein exhalation by the patient causes the flow control element to assume a second position to direct oxygen flow from the inlet to the exhaust;
  a pneumatic chamber, comprising a nozzle wherein inhalation by the patient reduces a pressure within the pneumatic chamber to a first pressure value and wherein exhalation by the patient increases the pressure within the pneumatic chamber to a second pressure value, wherein the second pressure value is larger than the first pressure value; and
  a sliding cap configured to slide between a first position and a second position, wherein a gap between the sliding cap and the nozzle of the pneumatic chamber is larger in the first position than in the second position.

2. The pneumatic system of claim 1, wherein the flow control element comprises a piston.

3. The pneumatic system of claim 1, wherein the system is configured for connection to an oxygen delivery mask.

4. The pneumatic system of claim 1, wherein when the pressure within the pneumatic chamber reaches the second pressure value, the flow control element is pushed into the second position.

5. The pneumatic system of claim 1, wherein inhalation by the patient causes the sliding cap to be sucked into the first position, thereby increasing the gap, thus reducing the pressure within the pneumatic chamber.

6. The pneumatic system of claim 1, wherein oxygen is supplied at a flow rate above 10 LPM.

7. The pneumatic system of claim 1, comprising a control unit configured to detect the position of the flow control element and to provide a signal indicative of the position.

8. An oxygen delivery system comprising:
  an oxygen delivery mask; and
  a pneumatic system configured to control delivering oxygen to the oxygen delivery mask, the pneumatic system comprising:
  an oxygen supply channel comprising an inlet, a patient delivery outlet in fluid flow communication with the oxygen delivery mask, and an exhaust; and
  a flow control element configured to control the flow from the oxygen inlet to the patient delivery outlet or to the exhaust;

a pneumatic chamber, comprising a nozzle wherein inhalation by the patient reduces a pressure within the pneumatic chamber to a first pressure value and wherein exhalation by the patient increases the pressure within the pneumatic chamber to a second pressure value, wherein the second pressure value is larger than the first pressure value; and a sliding cap configured to slide between a first position and a second position, wherein a gap between the sliding cap and the nozzle of the pneumatic chamber is larger in the first position than in the second position;

wherein inhalation by the patient causes the flow control element to assume a first position allowing oxygen to flow from the inlet to the patient delivery outlet and to the oxygen delivery mask; and wherein exhalation by the patient causes the flow control element to assume a second position directing oxygen flow from the inlet to the exhaust, thereby substantially preventing the oxygen flow from reaching the oxygen delivery mask.

9. The oxygen delivery system of claim 8, wherein the flow control element comprises a piston.

10. The oxygen delivery system of claim 8, wherein when the pressure within the pneumatic chamber reaches the second pressure value, the flow control element is pushed into the second position.

11. The oxygen delivery system of claim 8, wherein inhalation by the patient causes the sliding cap to be sucked into the first position, thereby increasing the gap, thus reducing the pressure within the pneumatic chamber.

12. The oxygen delivery system of claim 8, wherein oxygen is supplied at a flow rate above 10 LPM.

13. The oxygen delivery system of claim 8, comprising a control unit configured to detect the position of the flow control element and to provide a signal indicative of the position to a breath monitor.

14. The oxygen delivery system of claim 8, comprising a capnograph.

* * * * *